United States Patent [19]
Li et al.

[11] Patent Number: 6,066,123
[45] Date of Patent: May 23, 2000

[54] ENHANCEMENT OF BIOAVAILABILITY BY USE OF FOCUSED ENERGY DELIVERY TO A TARGET TISSUE

[75] Inventors: King Li, Stanford; Mark Bednarski, Los Altos, both of Calif.

[73] Assignee: The Board of Trustees of the Leland Stanford Junior University, Palo Alto, Calif.

[21] Appl. No.: 09/057,862

[22] Filed: Apr. 9, 1998

[51] Int. Cl.[7] .............................. A61N 7/00; A61B 5/055; A61K 9/127; A61K 48/00
[52] U.S. Cl. .............................. 604/507; 424/450; 514/2; 514/44; 600/411; 604/22
[58] Field of Search ........................... 514/44, 2; 604/22, 604/507; 424/450; 600/411

[56] References Cited

U.S. PATENT DOCUMENTS

| | | | |
|---|---|---|---|
| 4,767,402 | 8/1988 | Kost et al. | 604/22 |
| 4,948,587 | 8/1990 | Kost et al. | 424/435 |
| 5,115,805 | 5/1992 | Bommannan et al. | 601/2 |
| 5,247,935 | 9/1993 | Cline et al. | 600/411 |
| 5,267,985 | 12/1993 | Shimada et al. | 604/290 |
| 5,421,816 | 6/1995 | Lipkovker | 604/20 |
| 5,445,611 | 8/1995 | Eppstein et al. | 604/501 |
| 5,490,840 | 2/1996 | Uzgiris et al. | 604/22 |
| 5,614,502 | 3/1997 | Flotte et al. | 514/34 |
| 5,656,016 | 8/1997 | Ogden | 601/2 |
| 5,658,892 | 8/1997 | Flotte et al. | 514/44 |

OTHER PUBLICATIONS

Bao, Shiping, et al., "Transfection Of A Reporter Plasmid Into Cultured Cells By Sonoporation In Vtro," *Ultrasound In Med.& Biol.* (1997) vol. 23, No. (6):953–959.

Bednarski, Mark D., et al., "In Vivo Target–Specific Delivery of Macromolecular Agents With MR–Guided Focused Ultrasound[1]," *Radiology* (Jul. 1997) vol. 204, No. (1):263–268.

Tata, Darrell B., et al., "Selective Clinical Ultrasound Signals Mediate Differential Gene Transfer and Expression In Two Human Prostate Cancer Cell Lines: LnCap and PC–3" *Biochemical and Biophysical Research Communications* (1997) vol. 234:64–67; Article No. RC976578.

*Primary Examiner*—John S. Brusca
*Attorney, Agent, or Firm*—Bozicevic, Field & Francis LLP; Pamela Sherwood

[57] ABSTRACT

Targeted tissue in vivo is altered using focused energy to specifically control endothelial permeability and interstitial integrity. Image guidance may be used in combination with physical energy deposition to facilitate the targeted delivery of materials. The method of the invention serves as a platform for delivering pharmaceutical agents, nucleic acids, proteins, liposomes, etc. to cells.

19 Claims, 8 Drawing Sheets

(1 of 8 Drawing Sheet(s) Filed in Color)

ENHANCEMENT OF BIOAVAILABILITY BY USE OF FOCUSED ENERGY DELIVERY TO A TARGET TISSUE

BACKGROUND OF THE INVENTION

Traditional measures of bioavailability have focused on the ability to deliver a pharmaceutical agent to the blood stream. In fact, "bioavailability" is often defined as the concentration of a drug in the bloodstream after administration. This is misleading, however, because the blood, in most cases, is not the target tissue for drug action. The true site for drug action is often tissues outside of the vascular system, such as muscles, nerves, organs, etc. The actual concentration of a drug in the interstitial fluid surrounding target cells, and therefore in target cells, can be much lower than what is seen in the blood, because the vascular endothelium and tissue integrity forms a barrier to drug delivery.

Although some pharmaceutical materials can readily diffuse through all endothelial barriers and interstitial tissues, they often have a large volume of distribution and low target specificity, so that high doses are needed to achieve a therapeutic response. Many macromolecular pharmaceutical agents, including genetic materials, polypeptides, anti-sense polynucleotides, liposomes, and polymers used as drug carriers, are not effective in vivo due to their inability to penetrate the endothelial barrier and interstitial tissues and reach their target sites.

For example, possible therapeutic agents for diseases in the brain are often rendered useless because they cannot penetrate the blood brain barrier. Chemotherapy for the treatment of cancer is also dramatically altered by vascular permeability and tissue integrity. Liposomes loaded with doxorubicin are 20 times more effective than the free drug in Kaposi's Sarcoma because the liposomes can accumulate in the tumor due to "leaky" endothelium in the tumor vessels. Finally, key cytokines in the inflammatory process, such as tumor necrosis factor and interleukins, are involved in changing the permeability of the vasculature and delivery of pharmaceutical agents. These agents play a key role in the pathophysiology of ischemic and inflammatory diseases.

There is a need in the field for methods of preferential delivery of pharmaceutical agents to specific target tissues within the body. The present invention addresses this problem.

Relevant Literature

Bednarski et al. (1997) *Radiology* 204:263–268 discloses the targeted delivery of liposomes encapsulating gadopentetate dimeglumine into muscle tissue. Abstracts were published by Bednarski et al. (1996) disclosing the transfection of cultured cells with liposome encapsulated DNA using ultrasound.

Devices have been developed that focus ultrasonic sound waves at a focal point deep within tissues of a subject. At the focal point, energy is dissipated and local heating results. U.S. Pat. No. 5,247,935, "Magnetic resonance guided focused ultrasound surgery" discloses performance of surgery with a focused ultrasound transducer that selectively destroys tissue in a targeted region. A similar system for focused ultrasound is utilized in the methods of U.S. Pat. No. 5,490,840, which discloses methods of using localized heat to release drugs from carrier molecules at a target site.

U.S. Pat. No. 5,614,502 and U.S. Pat. No. 5,658,892, Flotte et al., disclose a method of increasing delivery of a compound across a cell membrane. The cell is exposed to a high pressure impulse that alters the membrane permeability in the presence of the target compound. A number of patents have issued relating to the use of ultrasound to deliver drugs to the skin, including: U.S. Pat. No. 5,445,611; U.S. Pat. No. 4,767,402; U.S. Pat. No. 5,267,985; U.S. Pat. No. 4,948,587; U.S. Pat. No. 5,115,805; U.S. Pat. No. 5,656,016; and U.S. Pat. No. 5,421,816.

Bao et al. (1997) *Ultrasound Med Biol* 23:953–959 report the transfection of a reporter plasmid into cultured cells by sonoporation. Tata et al. (1997) *Biochem Biophys Res Commun* 234(1):64–67 utilized low intensity ultrasound signals to mediate differential gene transfer and expression of a reporter plasmid in two human prostate cancer cell lines. Kim et al. (1996) *Hum Gene Ther* 7:1339–1346 transfected with plasmid DNA in vitro using ultrasound transmitted through the walls of cell culture flasks or plates.

SUMMARY OF THE INVENTION

Methods are provided for enhancing the delivery of a compound to a target tissue. The deposition of focused energy to a target tissue increases the ability of a compound to move through biological vessels and tissues. In this way the biologically useful concentration of a compound, i.e. the concentration immediately outside of targeted cell membranes, is increased. Image guidance may be used in combination with physical energy deposition to facilitate targeted delivery. Delivery to deep tissues, e.g. muscle, brain, liver, etc. is of particular interest.

BRIEF DESCRIPTION OF THE DRAWINGS

FIG. 1A and 1D are prior to any treatment. FIGS. 1B and 1E were obtained 1 hr after pulsed focus ultrasound (PFU) treatment and before Gd-liposome injection. FIGS. 1C and 1F were taken approximately 1 hr following Gd-liposome injection. The high signal intensity in the T2-weighted images seen in 1B and 1C are not observed prior to PFU treatment. Arrows in 1F highlight increased signal intensity not seen in the previous T1-weighted image 1E.

FIGS. 2A and 2D are prior to PFU exposure. T2- and T1-weighted images were obtained 1 hr (2B and 2E) and 2.5 hr (2C and 2F) following non-thermal PFU treatment. Arrow in 2C highlights high signal intensity area not seen in previous T2-weighted images. FIG. 2G was obtained approximately 1 hr following intravenous treatment with Gd-liposome. Arrow in 2G highlights high signal intensity area not seen in previous T1-weighted images.

FIG. 3A shows a representative section of muscle taken from a rabbit treated with Gd-liposome but not exposed to PFU. FIG. 3B shows a representative section of muscle taken from the high signal intensity area in the T1 weighted images. In FIGS. 3A and 3B thin and thick arrows denote normal and disrupted mitochondria, respectively. Asterisks (*) indicate areas of edema only seen on FIG. 3B, while "E" marks the endothelium of vessels in both 3A and 3B.

DESCRIPTION OF THE PREFERRED EMBODIMENTS

Figure 1A:
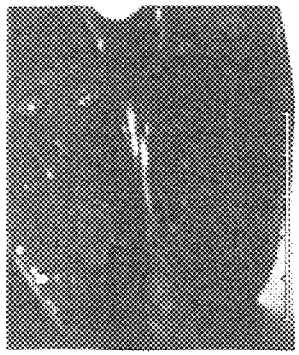
FIGS. 1A to 1F are T2- and T1-weighted MR images of the thighs of white male New Zealand rabbit treated under thermal conditions.
Figure 1B:
Figure 1C:
Figure 1D:
Figure 1E:
Figure 1F:

The in vivo delivery of biologically active compounds is enhanced by methods that modify targeted tissues, e.g. vessels comprising endothelial cells, and interstitial tissue. Focused energy, preferably image guided focused energy, is used to make a targeted tissue more available for movement of a compound of interest from within a vessel into the interstitial fluid of the tissue. The biologically useful concentration of compound in the target tissue is thereby increased.

Biological vessels, e.g. the vasculature of the circulatory system, such as arteries, veins, capillaries, etc.; trachea; renal and urethral tubules; fallopian tubes; eustachian tubes; etc. typically have an infrastructure of tightly joined endothelial or epithelial cells. The junctions between these cells permit passage of some materials, but are resistant to others. Biologically active compounds are easily administered by methods that utilize such vessels for systemic transport, for example by i.v. injection, but then suffer from difficulty in moving these compounds through the specific vessel walls of tissues of interest for treatment. Interstitial tissue can be highly resistant to the movement of biologically active compound, due to oncotic pressure, osmotic pressure, tight cellular junctions, tissue density, etc.

As used herein, the term "bioavailability" is not limited to measuring the concentration of a compound in the bloodstream, as it is often used in the art. The term is intended to refer to a biologically useful concentration of a compound. The biologically useful concentration is related to the amount of a compound that reaches its target site. For purposes of the subject invention, the actual target site will generally be a cell in body tissues. The biologically useful concentration is therefore related more closely to the compound concentration in the interstitial fluid immediately adjacent to a target cell, than it is to bloodstream concentration.

The subject methods apply focused energy to a target site, and induce changes in the cells and junctions of the vessel walls, as well as changes in the interstitial tissue properties. These changes make the targeted area temporarily more accessible to movement of exogenous compounds, and so the bioavailability of a circulating compound is increased, because more of the compound can reach the cells that are the site of action. The biologically useful concentration will usually be increased at least about one log by the subject methods, more usually at least about two logs, and often by three or four logs.

In contrast to previously described methods for mediating drug delivery with focused ultrasound, the subject methods are generally performed at energy levels below the threshold where permanent tissue damage is caused by heat resulting from the focused energy deposition. Heat damage may be assessed by various methods as known in the art, including gross histology, dosimetry, etc. (see Vykhodtseva et al. (1995) *Ultrasound in Med. & Biol.* 21:969–979). The actual energy level that is sufficient to cause permanent heat damage will vary with the specific tissue, but may be experimentally determined.

The methods are further distinguished by the timing of introducing the targeted agent. While one could administer an agent prior to the energy deposition step, it is not necessary. The changes in the targeted tissue are maintained for a period of time, and compounds of interest can be administered after the energy impulse is effected.

The method may be practiced with any mammalian species, including canines; felines; equines; bovines; ovines; etc. and primates, particularly humans. Animal models, particularly small mammals, e.g. murine, lagomorpha, etc. are of interest for experimental investigations.

The subject methods may utilize any method of focused energy deposition that is capable of enhancing the bioavailability of a compound through targeted changes to vessels and interstitial tissue. Suitable forms of energy include x-ray, ultrasound, thermal, laser or visible light, microwave or other radio frequency technology.

In a preferred embodiment of the invention, an ultrasound beam generated by piezoelectric transducers is focused to a volume as small as a cubic millimeter deep within tissues. By using focused ultrasound emitted in short high energy pulses, a regional shock wave is induced deep in tissue that alters tissue permeability without permanently damaging tissue. For example, an apparatus suitable for use in the subject methods is described in U.S. Pat. No. 5,247,935. A transducer of from about 0.1 to 5 MHz, usually from about 0.75 to 1.5 MHz, where the diameter can range from about 1 to 25 cm, more usually from about 5 to 15 cm, and the focal length can range from about 1 to 25 cm, more usually from about 5 to 15 cm, is exemplary. The level of energy delivered will generally be from about 0.01 to 100 watts/cm$^2$ at target, usually from about 0.1 to 100 watts/cm$^2$, for 0.01 msec to 100 msec using a duty cycle of from about 0.01 to 100 Hz, more usually from about 0.1 to 10 Hz.

In a preferred embodiment, image guidance is used in focusing the energy deposition to the desired target tissue. Methods of imaging are well-known in the art, and may include x-ray radiography, ultrasound, computer tomography, laser or visible light, microwave or other radio frequency technology. Exemplary of imaging is the use of magnetic resonance imaging, as shown in the examples.

Prior to, during, or following the focused energy deposition, the compound of interest is administered in a soluble form that will reach the targeted tissue via a vessel.

Administration may be achieved by any convenient method, including oral, buccal, rectal, parenteral, intraperitoneal, intradermal, transdermal, intracheal, intravenous, intra-arterial, etc. Often injection in the targeted region, e.g. intra-arterial or intravenous injection into blood vessels that feed into the targeted area, intra-muscular, or intra-tissue injection will be the delivery method of choice.

Tissues of interest include, but are not limited to, non-transformed tissues, e.g. muscle; organs such as kidney, liver, pancreas, islets of langerhans, neural and brain tissues; glands such as thyroid, parathyroid, paracrine glands, exocrine glands, and the like; and transformed or tumor tissues, e.g. solid tumors such as carcinomas, including cervical carcinoma, colorectal carcinoma, basal cell carcinoma, renal cell carcinoma, prostate carcinoma, small cell lung carcinoma, breast carcinoma; sarcomas, endotheliomas; mesotheliomas; etc.

The compounds delivered to the targeted tissue may be any biologically compatible exogenous agent, particularly agents that are not freely diffused into tissues under normal physiological conditions due to size, hydrophobicity, etc. Included are imaging agents, pharmacologically active drugs, genetically active molecules, etc. Larger compounds, ranging from about 10 nm to 200 nm or larger, include liposomes, e.g. anionic, cationic or neutral liposomes, which may encapsulate a variety of therapeutic agents; proteins, e.g. antibodies, cytokines, hormones, growth factors, etc.; nucleic acids, e.g. anti-sense oligonucleotides, plasmids, viral genomes, mRNA, etc.; viruses; sustained release drug implants, pro-drugs, pro-drug activators, etc. Also of interest is the delivery of a bolus of a compound that is otherwise freely permeable.

Compounds of interest include chemotherapeutic agents for neoplastic tissues, anti-inflammatory agents for ischemic or inflamed tissues, hormones or hormone antagonists for endocrine tissues, ion channel modifiers for cardiovascular or other tissues, and neuroactive agents for the central nervous system. Exemplary of pharmaceutical agents suitable for this invention are those described in The Pharmacological Basis of Therapeutics, Goodman and Gilman, McGraw-Hill, New York, New York, (1993) under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

The method of the invention can be exploited as a platform for delivery of genetic materials and thus is useful in a variety of applications. Nucleic acids that correct genetic deficiencies can be introduced into a targeted tissue, usually a solid tissue, e.g. pancreatic cells for the treatment of diabetes, liver cells to treat hepatic deficiencies, etc. Also of interest is the delivery of nucleic acids to accomplish genetic immunization. Genetic immunization involves delivery of a nucleic acid to cells for expression of the encoded immunogen within the target tissue. A preferred target tissue is muscle cells. An immune response against the immunogen is mounted in the animal, resulting in development of humoral and/or cellular immunity. Administration of nucleic acids according to the method of the invention, which results in genetic alteration of muscle cells and induction of an immune response can be used to elicit protective immunity.

The method of the invention is also useful in a variety of other settings in which genetic alteration of tissue is desirable. For example, the method of the invention can be used to introduce exogenous coding sequences into solid tumors, where the encoded gene product provides for recruitment of immune cells, induces apoptosis, inhibits angiogenesis, etc. in the tumor. Transgenic animals are created by transfection of targeted tissues with a nucleic acid of interest.

The nucleic acid materials for delivery to targeted tissue will usually comprise a nucleic acid of interest that encodes a gene product for which expression is desired, and a promoter for expression of the gene product. By "nucleic acid of interest" is meant any DNA, RNA or analog thereof that encodes a polypeptide or other gene product that is desirable for expression in tissue of a subject. The gene product can include a polypeptide, an anti-sense mRNA, or other gene product that is desirably expressed. The term "DNA of interest" or "DNA" is used herein as shorthand to refer to the nucleic acid of interest and is not meant to be limiting. The nucleic acid delivered to the tissue in vivo can take any number of forms. For example, the nucleic acid can be introduced as a linear or circular molecule, preferably a circular molecule (e.g., a circular plasmid or other construct).

The nucleic acid of interest and the promoter are operably linked to provide a construct, or vector for expression. Normally, "construct" will refer to a nucleic acid molecule that facilitates expression of a gene product encoded by the nucleic acid to be introduced. By "operably linked" is meant that a DNA sequence and a regulatory sequence(s) (e.g., a promoter sequence) are connected in such a way as to permit transcription when the appropriate molecules (e.g., transcriptional activator proteins) are bound to the regulatory sequence(s).

It will be recognized by those skilled in the art that the optimal quantity and spacing of individual dosages of nucleic acids will be determined by the precise form and components of the nucleic acid formulation to be delivered, the site of administration, the use to which the method is applied (e.g., immunization, treatment of a condition, production of transgenic animals, etc.), and the particular subject to which the nucleic acid formulation is to be delivered, and that such optimums can be determined by conventional techniques. It will also be appreciated by one skilled in the art that the optimal dosing regimen, i.e., the number of doses of nucleic acids, can be ascertained using conventional methods, e.g., course of treatment determination tests. Generally, a dosing regimen will involve administration of the selected nucleic acid formulation at least once, and may be performed multiple times over a period of days or weeks.

The amount of DNA to accomplish expression of a desired gene product at an effective level (e.g. a level effective to elicit an immune response, to alleviate a symptom of a condition or disease, etc.) will vary according to the desired effect (e.g. immunity, prophylaxis, tumor diminution, etc.), as well as with other variables such as the age of the subject, the tissue to be genetically altered, the gene product to be expressed and the desired level of its expression, etc. In general, the amount of DNA administered is an amount sufficient to provide for transformation of a number of cells that in turn provides for a level of gene product expression from the introduced DNA to provide for a desired effect. Dosages are routinely determined in the art, and can be extrapolated from the amounts of DNA effective in an animal mode (e.g., a rodent (mouse or rat) or other mammalian animal model), in which factors such as the efficiency of transformation and the levels of gene product expression achieved can be readily assessed and extrapolated to other vertebrate subjects. Generally speaking, the amount of DNA that is delivered to a human is usually on the order of about 100 times the amount of DNA effective in a rat.

The present invention is not limited to any particular nucleic acid coding for any particular polypeptide or other gene product, and the nucleic acid selected will vary with the aim the method is intended to accomplish, e.g. genetic immunization, delivery of a polypeptide for replacement or enhancement therapy, production of transgenic animals as models of a condition or disease, delivery of a gene for gene replacement therapy, etc. Exemplary gene products that can be expressed in genetically modified cells according to the invention are discussed in more detail below. Plasmids containing genes coding for a large number of physiologically active polypeptides and other gene products, as well as for antigens or immunogens, have been reported in the literature and can be readily obtained by those of skill in the art.

In a preferred embodiment, the nucleic acids of the invention encode a biologically active polypeptide, such as an immunity-conferring polypeptide, e.g. for genetic immunization, or a therapeutic polypeptide, e.g. for amelioration of a symptom associated with a polypeptide deficiency, or for reduction of a tumor. A polypeptide is understood to be any translation product of a nucleic acid regardless of size and glycosylation. The gene product can be any gene product that exhibits a desired biological activity, e.g. a functional characteristic such as enzymatic activity, or DNA binding; or structural characteristic such as role in cell architecture or presentation of one or more immunity-conferring epitopes in the host cell cytoplasm, nucleus, or membrane. Alternatively or in addition, the gene product may exhibit a desired biological activity following expression and secretion from the transformed cell.

Immunity-conferring polypeptides include those polypeptides that comprise an epitope that upon exposure to the immune system of a vertebrate (generally, a mammal), either alone or in the presence of a molecule that facilitates immune response induction (known in the immunology art as a carrier molecule), can act as an endogenous immunogen to provoke a humoral immune response, a cellular immune response, or both.

Any nucleic acid construct having a eukaryotic promoter operably linked to a DNA of interest can be used in the invention. For example, a bacterial plasmid, viral construct, or other DNA construct can be genetically engineered to provide a recombinant DNA molecule having a sequence encoding the desired gene product. Preferably the construct is capable of replication in both eukaryotic and prokaryotic hosts, which constructs are known in the art and are commercially available. The nucleic acid, or nucleic acid-containing construct, can be purified according to methods well known in the art and provided in a delivery formulation as described below.

The nucleic acid of interest can be obtained from any of a variety of sources or methods well known in the art, e.g. isolated from suitable cells, produced using synthetic techniques, etc., and the constructs prepared using recombinant techniques well known in the art. Likewise, techniques for obtaining expression of DNA or RNA sequences in a genetically altered host cell are known in the art (see, for example, Kormal et al., *Proc. Natl. Acad. Sci. USA*, 84:2150–2154, 1987; Sambrook et al. *Molecular Cloning: A Laboratory Manual*, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Preferably, the DNA construct contains a promoter to facilitate expression of the DNA of interest. The promoter used will vary with the intended aim of the method of the invention. For example, where the method is to be used to accomplish genetic immunization or treatment of tumors, the promoter may be a strong, constitutive eukaryotic promoter such as a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., *Cell* 41:521–530,1985) and the promoter from the long terminal repeat (LTR) of RSV (Gorman et al., *Proc. Natl. Acad. Sci. USA* 79:6777–6781, 1982).

Sequences of many of the gene products desirable for delivery according to the method of the invention are known. The sequences have been described in the literature, are available in public sequence databases such as GenBank, or are otherwise publically available. With the availability of automated nucleic acid synthesis equipment, both DNA and RNA can be synthesized directly when the nucleotide sequence is known, or synthesized by PCR cloning followed by growth in a suitable microbial host. Moreover, when the amino acid sequence of a desired polypeptide is known, a suitable coding sequence for the nucleic acid can be inferred. Where the DNA encoding a gene product of interest has not been isolated, this can be accomplished by various, standard protocols well known to those of skill in the art (see, for example, Sambrook et al., ibid; Suggs et al. 1981 *Proc. Natl. Acad. Sci. USA* 78:6613–6617; U.S. Pat. No. 4,394,443; each of which are incorporated herein by reference with respect to identification and isolation of DNA encoding a gene product of interest).

Expression of the introduced nucleic acid can be short-term, i.e. a few hours to several hours to a few days, or permanent or long-term i.e. from a week to several weeks to a few months or more. In general, gene product expression from the introduced nucleic acid ranges from at least about 1 to 2 days, or 3 to 5 days, to about 1 week, generally about 1 to 4 weeks, up to about 6 weeks, and may be as long as about 10 to 12 weeks or longer. The short-term nature of gene product expression can be due to loss of the introduced nucleic acid, inactivation of the nucleic acid, and/or natural maturation and sloughing off of the transformed cell. Where expression times of more than a few weeks are desired, for example from about 10 to 12 weeks or longer, expression of the gene product can be maintained by using a retroviral construct having inactivated LTRs and an internal promoter in the construct to drive gene product expression.

Various conditions, diseases, and/or symptoms thereof are amenable to treatment via the biological effect of a gene product delivered to the subject using the methods of the invention. The specific gene product delivered using the method of the invention will, of course, vary with the condition, disease, or symptom from which the subject desires relief. Exemplary conditions and diseases, as well as their attendant symptoms, that are amenable to treatment by expression of an appropriate gene product in the targeted tissue(e.g., subsequent to introduction of DNA encoding the gene product using the method of the invention) include both cell specific and systemic diseases. These diseases can be grouped into several categories including, but not limited to, single gene congenital diseases, multifactorial acquired diseases, tumors, and systemic diseases (e.g., diseases of inadequate or poorly controlled circulating levels of specific polypeptides).

It is to be understood that this invention is not limited to the particular methodology, protocols, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a muscle cell" includes a plurality of such cells and reference to "the construct" includes reference to one or more constructs and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

EXAMPLES

The following examples are put forth so as to provide those of ordinary skill in the art with a complete disclosure and description of how to carry out the invention and are not intended to limit the scope of what the inventors regard as their invention, nor are they intended to represent or imply that the experiments below are all of or the only experiments performed. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, and temperature is in degrees Centigrade.

Example 1
Delivery of Biotinylated Liposomes Encapsulating Gadopentetate Dimeglumine
Materials and Methods:

A polymerized liposome particle that incorporates gadolinium ions in its interior and biotin on its surface was constructed from 1,2-bis(10,12-tricosadiynoyl)-sn-glycero-3-phosphocholine and 0.5% of a biotinylated phosphotidylcholine lipid in a 500 mM solution of gadopentetate dimeglumine (Berlex, Wayne, N.J., USA). The incorporation of pharmaceutical agents in the liposome is represented here by the encapsulation of gadopentate dimeglumine and the delivery of covalently bound agents is represented by the biotin substrate attached to the surface of the particle. The desired Gd-liposome was purified by gel filtration chromatography (Sephadex G-25). These liposomes were found to have a diameter of 102 nm with a SD of 16.8 nm by light scattering measurements (Coulter N4+, Miami, Fla., USA). Aliquots of Gd-liposomes (4 ml of a pH 7 aqueous solution, 20 mM total lipid) were prepared as described above and used for the following experiments.

In preparation for ultrasound treatment, the animals were anesthetized and intubated in compliance with Stanford University animal facility protocol (5 mg/Kg Rompin and 35 mg/Kg Ketamine injected subcutaneously followed by approximately 1.5–2.0% halothane in 100% oxygen). The thigh of the animals were shaved, cleaned and placed in the MR/FU apparatus. Images were obtained on a 1.5 T General Electric MR scanner (Milwaukee, Wis.) using a T2-weighted fast spin echo pulse sequence with a repetition time (TR) of 4000 ms, effective echo time (TEeff) 105 ms, 2 excitations (NEX) and a 256×256 matrix and a T1 weighted spin echo pulse sequence with TR 300 ms, TE 18 ms, 2 NEX and a 256×256 matrix and detection was accomplished using a surface coil (General Electric 5 inch GP coil) placed on the thigh. Skeletal muscle was chosen for these studies because of its extremely low intrinsic microvascular permeability to macromolecules.

Photoacoustic spectroscopy was performed with an Optison analyzer (Intec, Sunnyvale, Calif.) to characterize the quality, size and location of the focal zone of the ultrasound transducer(10 cm diameter, 1.56 MHz Ultrasonic Devices, Milpitas, Calif.) in vitro. The transducer was found to generate an ultrasonic sine wave with an ellipsoid focal zone of approximately 2 mm×2 mm×5 mm located approximately 6.2 cm from the transducer edge and 7.7 cm from the transducer center. The transducer was powered at 10 V for these measurements. The location of the focal zone was determined in vivo in the MR scanner using T2-weighted imaging following focused ultrasound treatment of a thigh of a New Zealand rabbit for 5 minutes. The transducer was powered continuously at 280 mV amplified by a 50 dB RF power amplifier (ENI model 2100L, Rochester, N.Y.) giving 35 W.s/79 $cm^2$ with a focusing factor of 1600 resulting in a dose peak intensity at the focal point of approximately 700 W .s/$cm^2$.

For the Gd-liposome targeting experiments, the acquisition of T2- or T1-weighted images were obtained prior to and after pulsed-focused ultrasound treatment and following subsequent Gd-liposome treatment. The pulsed-focused ultrasound (PFU) was applied to the thigh muscle under two ultrasound parameter sets as outlined in Table 1: a) The transducer was powered at 280 mV amplified by a 50 dB RF amplifier for 100 ms with a duty cycle of 1 Hz for a total of 5 min. These conditions yield a maximal delivered dose of 70 W$^*$s/$cm^2$ (Table 1, Parameter set A). This value is based on the maximum delivery of 35 W from the amplifier to a transducer area of 79 $cm^2$ with a focusing factor of 1600. b) The transducer was powered at 990 mV amplified by a 50 dB RF amplifier for 100 µs with a duty cycle of 1 Hz for a total of 5 min. These conditions yield a maximal delivered dose of 1.0 W.s/$cm^2$ (Table 1, Parameter set B). This value is based on the maximum delivery of 500 W from the amplifier to a transducer area of 79 $cm^2$ with a focusing factor of 1600.

TABLE 1

Comparison of two Focused Ultrasound Parameter sets on MR enhancement post Gd-Liposome Injection

| Parameter set | Duty cycle (ms) | Total Energy W · s/cm2 | Focal Zone Enhancement | |
|---|---|---|---|---|
| | | | T2-weighted | T1-weighted |
| A (N = 3) | 10 | 70 | ++++ | 1 |
| B (N = 1) | 0.1 | 1 | +++ | +++ |

Transducer Frequency, 1.56 MHz

Representative transmission electron micrographs of muscle biopsies were taken within 1.5 hours following the liposome injection from the thighs of rabbits used as a control (intravenous Gd-liposome without PFU treatment) and from the rabbits treated with short-pulsed, high-power focused ultrasound and intravenous Gd-liposome. Tissue biopsies were taken after sacrificing the animals and the location of the irradiated area was demarcated by the placement of a MR compatible biopsy needle adjacent to the treated region. Correct placement was confirmed by T2-weighted image analysis. The tissue was then prepared by standard procedure and analyzed on a Philips EM-201 with an acceleration voltage of 60 kV.

Histochemical staining for the presence of biotin was performed using either gold labeled streptavidin with silver enhancement for light microscopy (Ted Pella Inc., Redding, Calif.) or streptavidin-b-galactosidase using X-Gal as a detection system. The samples were taken from the same sections as those used in the TEM studies.

Figure 3A:
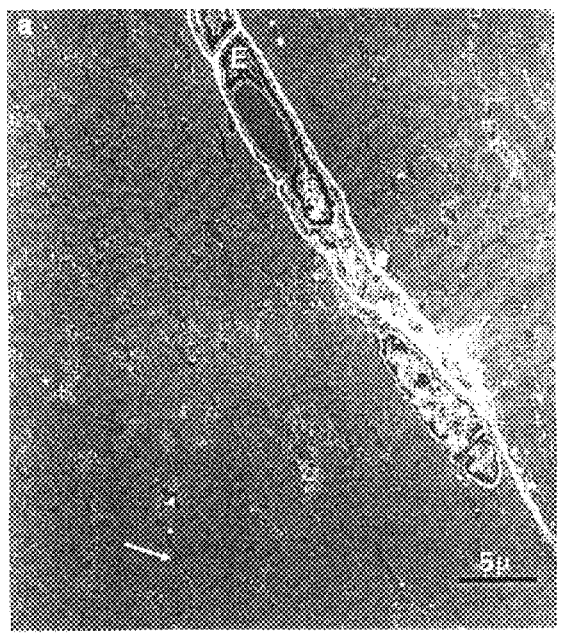
FIGS. 3A and 3B are transmission electron microscopy (TEM) of tissue biopsies taken from the thighs of white male New Zealand rabbits (magnification 5500×).
Figure 3B:
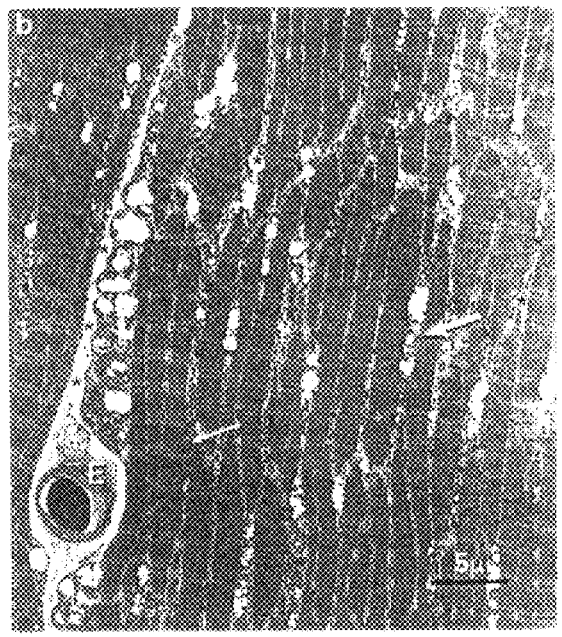
Figure 4:
FIG. 4 shows Fat Saturated T2 Weighted Fast Spin Echo (TR/TE4000/105, Echo Train Length=8, 256×256 matrix, NEX=2) magnetic resonance image demonstrating two hyperintense areas in the left thigh of a rabbit. The hyperintense areas represented edema induced by focused ultrasound irradiation.
Figure 5:
FIG. 5 shows the corresponding T1 Weighted Spin Echo (TR/TE 300/18, 256×256 matrix, NEX=2) magnetic resonance image approximately 4 hours after intravenous injection.

Results:

The results are summarized in table 1 and FIGS. 3–5. Table 1 shows that for both thermal and non-thermal energy deposition conditions (parameterset A and B), there was a resultant increase in signal intensity as seen in the T2-weighted image after PFU treatment. No change in signal intensity was observed in the T1 weighted image in the focal zone under these conditions. After the injection of Gd-liposome, an increase in T1-weighted contrast enhancement is observed in both cases. Higher energy deposition (Parameter set A) resulted in greater increase in signal intensity in the T2-weighted image than the lower energy condition (Parameter set B). However, T1 weighted contrast enhancement due to Gd-liposome is greater in the case of the non-thermal energy deposition pattern (Parameterset B). Note that in Parameterset B the power is delivered in very short, high intensity pulses.

FIGS. 1a to 1f contain T2- and T1-weighted MR images of the thighs of a white male New Zealand rabbit prior to any treatment (1a and 1d) and following pulsed focused ultrasound treatment (Parameter set A Table 1) at 1 hr (1b and 1e), and 0.5 hr following intravenous treatment with Gd-liposome (1c and 1f). In FIG. 1, the immediate appearance of the bright zone in the T2-weighted image (1b) is consistent with extensive changes in muscle morphology as these conditions result in a delivered energy dose of 70 W.s/cm$^2$ which is well above the 1.5 W.s/cm$^2$ threshold for thermal ablation of tissue. These values are reported in dosage form so that the pulsed-mode ultrasound experiments can be compared to continuous-mode data reported in the literature for thermal ablation. In contrast to the dramatic immediate increase in signal intensity of the T2-weighted image, the accumulation of Gd-liposome at 0.5 hr post Gd-treatment is low (arrows in 1f and table 1).

FIG. 2 contains T2- and T1-weighted MR images of the thighs of a white male New Zealand rabbit prior to any treatment (2a and 2d) and following PFU (Parameter set B Table 1) at 1 hr (2b and 2e), 2 hr (2c and 2f, and 0.5 hr following intravenous treatment with Gd-liposome (2g). After 1 hr post focused ultrasound treatment, little appreciable change was observed in the T2- or T1-weighted images as seen in FIG. 2b and 2e, respectively. This is in sharp contrast to conditions of higher energy deposition (70 W.s/cm$^2$, Parameter set A Table 1) where the increase in signal intensity of the T2-weighted image was immediate (2b). After a total elapsed time of 2.5 hr following PFU treatment, a bright region became evident in the T2-weighted image 2c (117% higher signal intensity compared to adjacent muscle) at the focal zone of the transducer (see arrow in image 2c). Signal intensity of pulsed FU treated area on T2-weighted image 2.5 hours post-treatment was 72.1:19.3, and the signal intensity of the adjacent untreated muscle was 33.2:11.1. No change is seen in the T1-weighted image 2f. At this point, the rabbit was injected intravenously with Gd-liposome. Approximately 30 minutes following the liposome injection, enhancement in the T1-weighted image was observed (48% increase in signal intensity compared to pre-contrast image 2f) in the same region as the edema observed in the T2-weighted image 2c (see arrow in image 2g). Signal intensity of pulsed FU treated area on T1-weighted image before injection of Gd-liposome was 136.2:14.9, and the signal intensity increased to 201.3:24.6 post-Gd-liposome injection. Both measurements were obtained with the same Region of Interest (36 mm$^2$ in size). This focal increase in signal intensity in the T1-weighted image is due to the accumulation of the Gd-liposomes in the FU-treated region. In related studies we have noted that the high signal intensity that appears in the T2-weighted images following pulsed FU treatment disappears after a week.

Figure 2A:
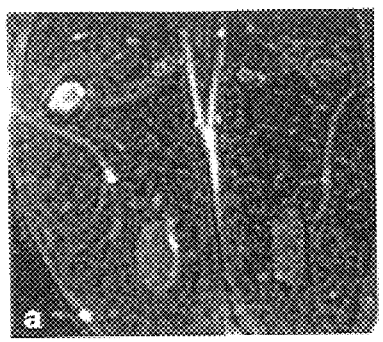
FIGS. 2A to 2G are T2- and T1-weighted MR images of the thighs of white male New Zealand rabbit.
Figure 2B:
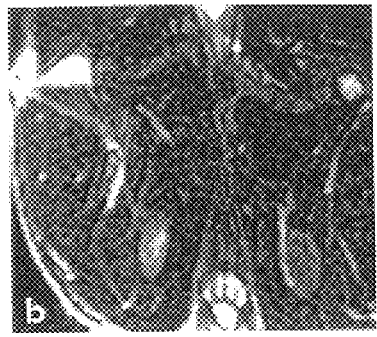
Figure 2C:
Figure 2E:
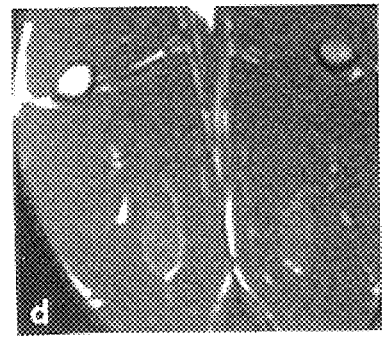
Figure 2D:
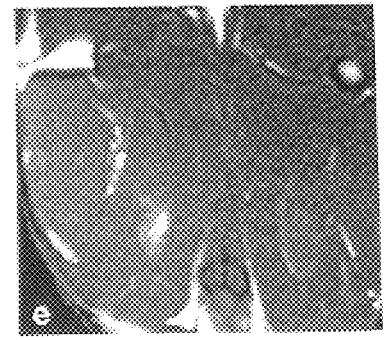
Figure 2F:
Figure 2G:
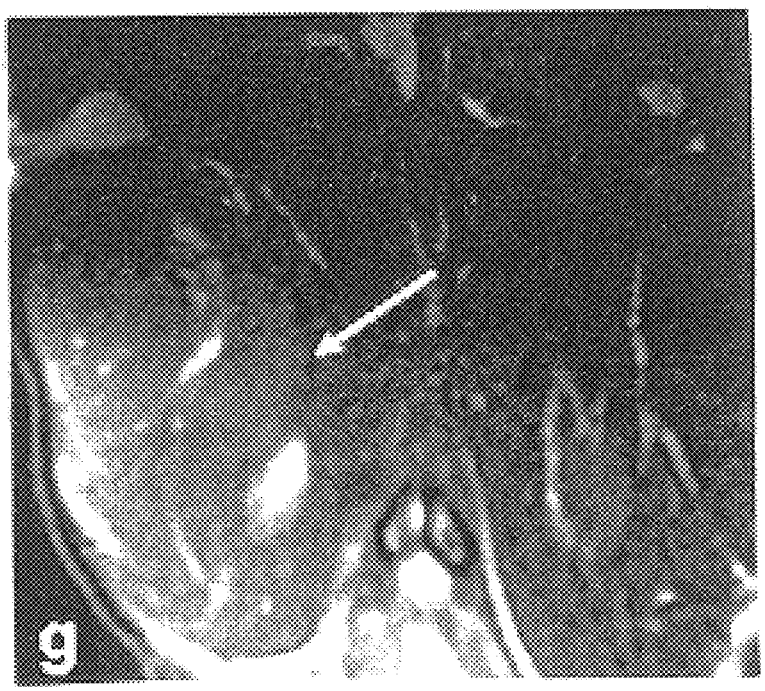

In adjacent muscle outside the focal zone of the PFU, signal intensity increased from 103.3:12.1 pre-Gd-liposome injection to 136.0:11.0 post-injection. This is due to the recirculating Gd-liposome which acts as a blood-pool T1 contrast agent. Although background enhancement is observed due to blood pool effects, no focal T1-weighted contrast enhancement was observed in the muscle of controls that were treated with Gd-liposomes without FU treatment or in animals treated with FU without Gd-liposomes. The relatively higher signal intensity close to the surface of the thigh is due to the effects of the surface coil and is evident on both pre- and post-Gd-liposome injection images (FIGS. 2f and 2g).

FIG. 3 shows the representative TEM of tissue biopsies. The TEM of the control rabbit (3a) has normal appearing vascular endothelium and the muscle is not edematous. The TEM of the rabbit treated with pulsed FU as described above (3b) has endothelium that appears intact (E) but altered and the muscle is edematous and the integrity altered as the fibers are moved apart. Close examination of the mitochondria within the muscle finds many intact (small arrows) with a large fraction that are swollen and with the cristae disrupted (large arrow). Histochemical staining for the presence of biotin using labeled streptavidin indicates that the Gd-liposomes that are biotinylated are present in the muscle samples treated with FU.

Discussion:

The location of the FU focal zone can be controlled by correct placement of ultrasound transducer as determined by photoacoustic spectroscopy and by T2 weighted MR imaging. Photoacoustic spectroscopy was used to determine the distance of the focal zone from the transducer in vitro. This value could be accurately reproduced in vivo as shown by the occurrence of T2 weighted changes at the same distance from the transducer.

MR guided focused-ultrasound using energy deposition values below that for thermal tissue damage, shows the capability to alter the endothelium to allow passage of macromolecular structures (100 nm) into the focal region. FIG. 2 clearly shows the accumulation of Gd-liposome in the T1-weighted image (arrow in 2g) in the same region as the change in T2-weighted image due to edema (arrow in 2c). In these experiments, energy deposition was 1 W.s/cm$^2$ (Parameterset B, Table 1) and is below the theoretical threshold for thermal ablation (1.5 W.s/cm$^2$). Increasing the energy deposition to 70 W.s/cm$^2$ (Parameterset A) causes immediate and intense change in the T2 weighted image which is in contrast to that observed when the energy deposition was 1 W.s/cm² (compare FIGS. 1b with 2b). Also, the focal T1-weighted contrast enhancement due to Gd-liposome accumulation is less than that observed for Parameter set B (compare FIGS. 1f to 2g). This observation may be due to changes in the vessels that prevent leakage of the macromolecular agent.

MR guided biopsies and analysis by TEM confirmed the presence of edema that were absent in control muscle not treated with PFU (Parameter set B). Perturbations in the endothelium are also observed when compared to control tissue ("E" in 3a and 3b), as well as disruption of the mitochondria in treated tissues (arrows in 3a and 3b) and changes in muscle integrity. In related experiments rabbits were imaged 7 days post FU-treatment, no hyperintensity was observed in the treated regions by T2 weighted imaging. Thus, the changes in the tissue structure do not seem to be permanent.

In conclusion, these observations support the hypothesis that MR guided pulsed-focused ultrasound can cause changes in the endothelial barrier and tissue integrity that can be used to target macromolecules into defined regions deep into tissues. The tissue changes observed on T2 weighted imaging and the accumulation of the Gd-liposomes in the FU treated regions seem to be a function of the total energy deposition, the duty cycle and the power of the FU pulse. In the case of low energy deposition these changes seem to be reversible. Thus, pulsed-focused ultrasound, together with magnetic resonance imaging as the guidance mechanism, offers a new vehicle for the delivery of macromolecular chemotherapeutic agents and other pharmaceutical molecules to desired tissues.

Example 2
Paramagnetic Liposome Mediated Delivery

Liposomes containing gadolinium ions were constructed as described in U.S. Pat. No. 5,512,294; Storrs et al. (1995) J. Am. Chem. Soc. 117:7301–7306; and Storrs et al. (1995) J. Mag. Res. Imag. 5:719–724. The liposome particles used in these demonstrations had average particle sizes ranging from about 100 to 200 nanometers, as determined by dynamic light scattering (Coulter N4+). An aqueous solution of the paramagnetic polymerized liposomes comprising 85% PDA and 15% DTPA-bis (PEG-PDA)diamide Gadolinium; 30 mM in total lipid (pH 7) was used for one system while cationic liposomes were used for plasmid delivery and anionic liposomes for ecapsulation of pharmaceutical agents were used for examples of pharmaceutical agent delivery as described above.

Figure 8:
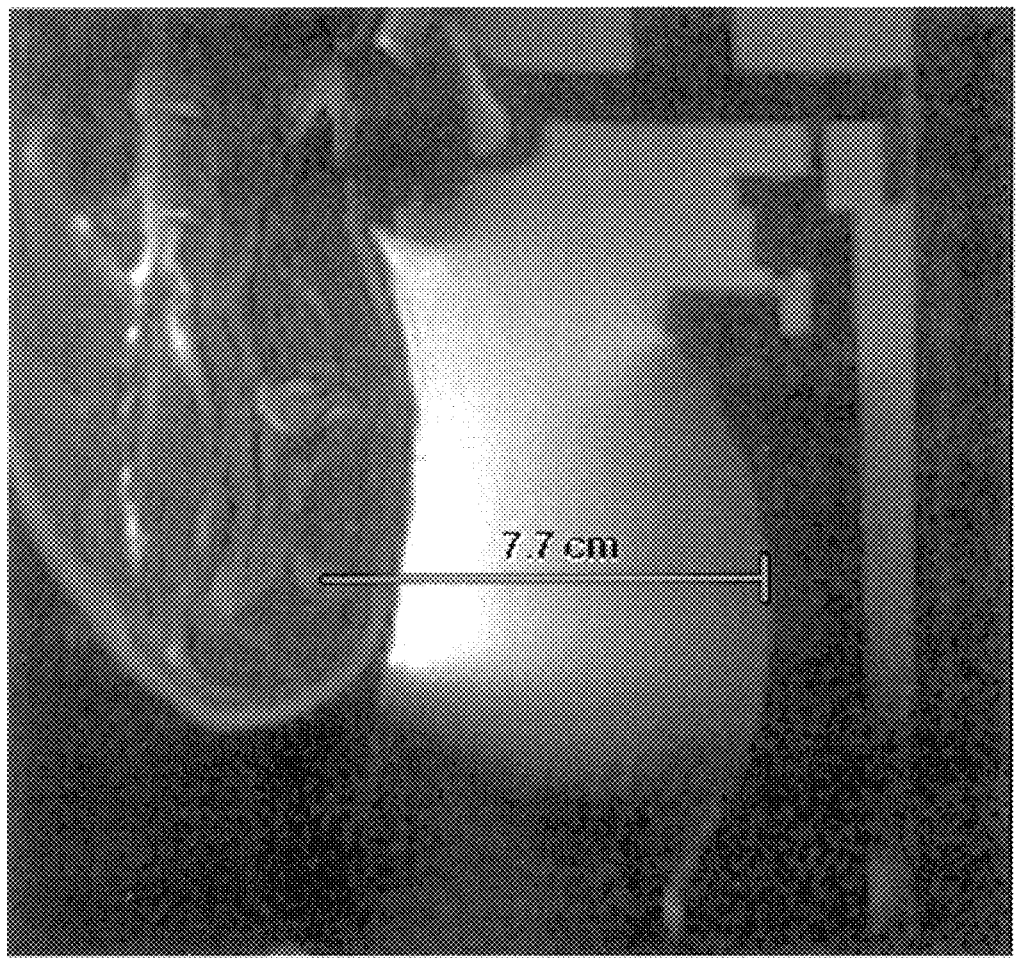
FIG. 8 is a magnetic resonance image showing the magnetic resonance image guided focused ultrasound system as used in the subject invention. The hyperintense area in the rabbit thigh muscle, indicated by the arrow, is shown by this Fat Saturated T2 Weighted Fast Spin Echo (TR/TE 4000/105, Echo Train Length 8, 256×256 matrix, NEX=2) image to be in the expected focal zone of the transducer, as indicated by the line labeled 1 from the center of the transducer, labeled 2. The location of the focal zone was confirmed by acoustic-optic scattering.

In the following examples, prior to injection of the above prepared aqueous solution of paramagnetic polymerized liposomes intravenously delivered to rabbits, T2 weighted magnetic resonance images of the target area of the left thigh were obtained. The T2 weighted magnetic resonance image was used to place the focused ultrasound beam into the desired area using the transducer as shown in FIG. 8. FIG. 4 shows Fat Saturated T2 Weighted Fast Spin Echo (TR/TE4000/105, Echo Train Length=8, 256×256 matrix, NEX=2) magnetic resonance image demonstrating two hyperintense areas in the left thigh of a rabbit. The hyperintense areas represented edema induced by focused ultrasound irradiation. The more superior hyperintense area, indicated by the large arrow, was irradiated with focused ultrasound using a 10 cm diameter 1.5 MHZ transducer at 40 W, duty cycle of 1 Hz, 500 msec on time for 5 minutes and the more interior hyperintense area, indicated by the small arrow, was irradiated with the same transducer at 80 W, duty cycle of 1 Hz, 500 msec on time for 20 minutes.

Following the focused ultrasound irradiation, 4 ml of the above described 30 mM paramagnetic polymerized liposome preparation, amounting to 0.015 mmol/kg Gd (85% PDA and 15% DTPA-bis (PEG-PDA) diamide gadolinium was injected intravenously into male New Zealand white rabbits.

Approximately 4 hours after the intravenous injection, corresponding T1 Weighted Spin Echo (TR/TE 300118, 256×256 matrix, NEX=2) magnetic resonance image was made using a 1.5T General Electric magnetic resonance scanner, and is shown in FIG. 5. Notice the enhancement corresponding to the more superior hyperintense area, indicated by the arrow, after the contrast agent injection.

Example 3
GD-DTPA Delivery

Figure 6:
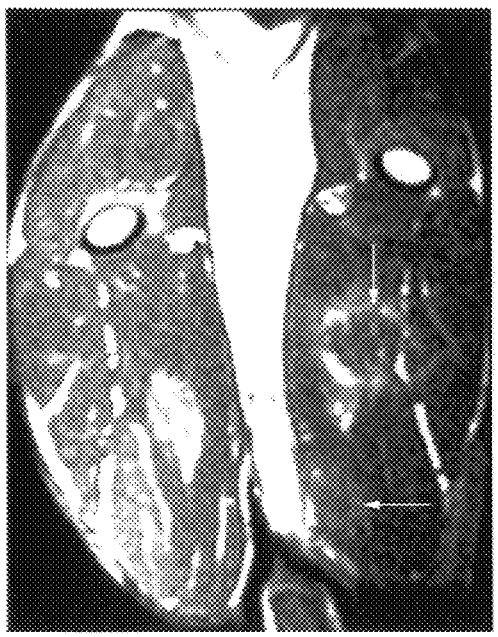
FIG. 6 is a T1 Weighted Spin Echo (TR/TE 300/18, 256×256 matrix, NEX=2) magnetic resonance image made immediately after an intravenous injection of 0.1 mmol/kg of Gd-DTPA.
Figure 7:
FIG. 7 is a T1 Weighted Spin Echo magnetic resonance image made five minutes after the injection of 0.1 mmol/kg Gd-DTPA

In accordance with the above methods, an intravenous injection of 0.1 mmol/kg of Gd-DTPA, about I to 5 nanometers, was made and immediately thereafter a T1 Weighted Spin Echo (TR/TE 300/18, 256×256 matrix, NEX=2) magnetic resonance image was made and is shown as FIG. 6. Notice the enhancement corresponding to both hyperintense areas, indicated by the arrows. Five minutes after the injection of 0.1 mmol/kg Gd-DTPA a T1 Weighted Spin Echo magnetic resonance image was made under the same conditions and is shown in FIG. 7. Notice that further enhancement is seen in both areas.

FIG. 8 is a magnetic resonance image showing the magnetic resonance image guided focused ultrasound system as used in the above work. The hyperintense area in the rabbit thigh muscle, indicated by the arrow, is shown by this Fat Saturated T2 Weighted Fast Spin Echo (TR/TE 4000/105, Echo Train Length=8, 256×256 matrix, NEX=2) image to be in the expected focal zone of the transducer, as indicated by the line 7.7 cm from the center of the transducer. The location of the focal zone was confirmed by acoustic-optic scattering. Focused ultrasound was produced by a transducer that put out spherically focused ultrasonic sine waves with a frequency of 1.5 MHz and a focal spot of about 1 mm×1 mm×3mm in size. The transducer was powered by a 50 dB RF power amplifier, an INE 2100L.

Example 4
Liposome Directed Gene Delivery

In like manner, an aqueous solution of paramagnetic liposome-plasmid conjugates (47% DOTMA, 47% cholesterol) and 6% PEG-PDA, 3 mM in total lipid containing approximately 2.5 mg DNA, was prepared, average size of 600 to 700 nanometers, and injected intravenously into a male New Zealand white rabbit. The animal was anesthetized and intubated using standard procedures, 5 mg/Kg Rompin and 35 mg/Kg Ketamine injected subcutaneously followed by approximately 1.50–2.0% Halothane and oxygen after intubation. Prior to the paramagnetic liposome-plasmid conjugate injection, T2 weighted magnetic resonance images, TR/TE 4000/105 msec, were obtained and used to place the focused ultrasound beam into the desired location. Focused ultrasound, 1.5 MHz, focal spot 1 mm×1 mm×3 mm, was applied to the thigh at 35 watts delivered for 500 msec at a rate of 1 Hz for 20 minutes. T1 weighted magnetic resonance images, TR/TE 300/18 msec, and T2, weighted magnetic resonance images, TR/TE 4000/105 msec, were obtained immediately after, and approximately 1 hour after the focused ultrasound. At 1 hour post ultrasound irradiation, significant magnetic resonance image T1 enhancement was observed at the ultrasound irradiated site when paramagnetic liposome-plasmid conjugates were administered. In all instances when ultrasound irradiation was applied, T1 weighted magnetic resonance images showed increase in signal intensities in the irradiated regions indicating that the plasmid-liposome conjugates were accumulated in the irradiated region. The muscle not irradiated with focused ultrasound showed no T1 enhancement.

Example 5
GD-DTPA Encapsulated Liposome Delivery

In another example, Gd-DTPA, about 10 nanometers, was encapsulated in the interior of liposomes by using 300 mM Gd-DTPA solution when preparing the liposomes. The liposomes were purified by gel filtration chromatography and injected intravenously into a male New Zealand white rabbit. The animal was anesthetized and intubated using standard procedures, 5 mg/Kg Rompin and 35 mg/Kg Ketamine injected subcutaneously followed by approximately 1.50–2.0% Halothane and Oxygen after intubation. Prior to the encapsulated liposome injection, T2 weighted magnetic resonance images, TR/TE 4000/105 msec, were obtained and used to place the focused ultrasound beam into the desired location. Focused ultrasound, 1.5 MHz, focal spot 1 mm×1 mm×3 mm, was applied to the thigh at 35 wafts delivered for 500 msec at a rate of 1 Hz for 20 minutes. T1 weighted magnetic resonance images, TR/TE 300/18 msec, and T2 weighted magnetic resonance images, TRITE 4000/105 msec, were obtained immediately after, and approximately 1½ hours after the focused ultrasound. At 1½ hours post ultrasound irradiation, significant magnetic resonance image T1 enhancement was observed at the ultrasound irradiated site when Gd-DTPA encapsulated liposomes were administered. In all instances when ultrasound irradiation was applied, T1 weighted magnetic resonance images showed increase in signal intensities in the irradiated regions indicating that the Gd-DTPA encapsulated liposomes were accumulated in the irradiated region. The muscle not irradiated with focused ultrasound showed no T1 enhancement.

The above examples show that focused ultrasound irradiation used in conjunction with magnetic resonance image tracking is effective to induce target specific changes in the endothelial barrier to allow passage of particles in the size range of 1 to about 1000 nanometers to be passed specifically into the ultrasound irradiated region. The paramagnetic polymerized liposomes can be visualized and the delivery quantified using standard T1 weighted magnetic resonance imaging sequences while T2 magnetic resonance images are effectively used to position the ultrasound beam to the desired location prior to injection of the particles. The focused ultrasound irradiation resulted in no gross morphological changes in the tissues. This approach provides a new vehicle for the delivery of pharmaceutical agents to specific tissues using blood-pool carriers, such as liposomes or liposome-drug complexes or low molecular weight pharmaceutical agents and focused ultrasound in conjunction with magnetic resonance imaging.

Example 6
Delivery of Genetic Material

Magnetic resonance guided focused ultrasound is used as a new method to deliver plasmid DNA for applications in gene delivery to specific target tissue in vivo.

Materials and Methods

DNA vector. The plasmid pEGFP-N1a N-terminal protein fusion vector (Clontech Laboratory, Inc., Palo Alto, Calif.) was used as the marker for gene delivery. Its expression can be easily visualized using fluorescence microscopy. pEGFPN1 is a 4.7 kb plasmid that encodes a green fluorescent protein (GFP) that is optimized for high expression in mammalian cells. Fusions can be made into to the N-terminus of EGFP and retain the fluorescent properties of the native protein allowing the localization of the fusion protein in vivo.

Desired tissue areas, as determined by magnetic resonance imaging, were irradiated with focused ultrasound energy (1.5 MHz transducer with 10 cm diameter and 10 cm focal length) in an amount (35 watts for 100–500 msec on duty cycle of 1 Hz for 3–20 min.) directed to the thigh to modify the endothelial layer and interstitial tissues to allow passage from blood on one side of the endothelium into the targeted tissue volume on the opposite side of the endothelium and then move through the interstitial tissues.

The transducer generated a spherically focused ultrasound sine wave located approximately 7.7 cm from the transducer center. The thigh of a male white New Zealand rabbit under anesthesia was subjected to focused ultrasound treatment. This treatment involved exposing the thigh for five minutes with transducer power at 250 mV amplified by a 50 dB RF power amplifier for 100 ms with a duty cycle of 1 Hz. These conditions yield a maximum dose at the focal point of approximately 70 W/cm$^2$. Immediately after this treatment a region of high signal intensity appeared in the thigh muscle on T2 weighted images (FSE 4000/120). At this point the rabbit was injected intra-arterially with 4 ml of aqueous solution (pH 7.0) containing 4.5 mg of the pEGFP-N1 plasmid vector, via a femoral arterial catheter into the treated thigh.

The animal was sacrificed after three days and the region of interest was removed, fixed in 10% formalin, embedded in paraffin, sliced at 6 μm sections and analyzed using fluorescence microscopy. GFP has an excitation at 488 nm and an emission at 507 nm. As a control the experiment was repeated in another animal without focused ultrasound treatment.

Figure 9:
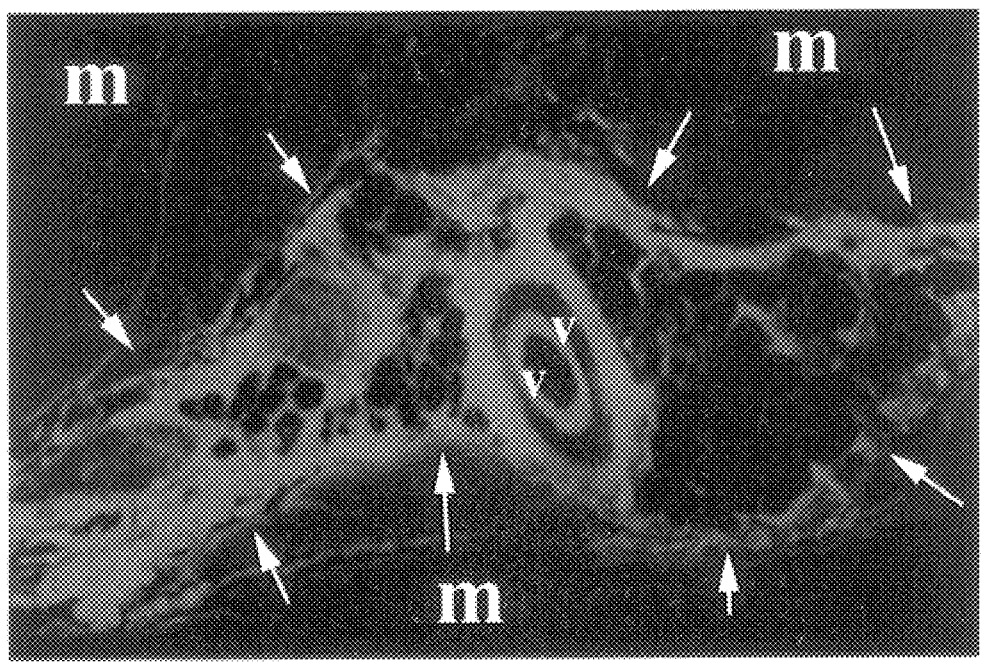
FIG. 9 is a representative fluorescence microscopic images of a control specimen at 100× magnification, showing the expression of GFP only in vessel walls and the immediately surrounding soft tissues.
Figure 10:
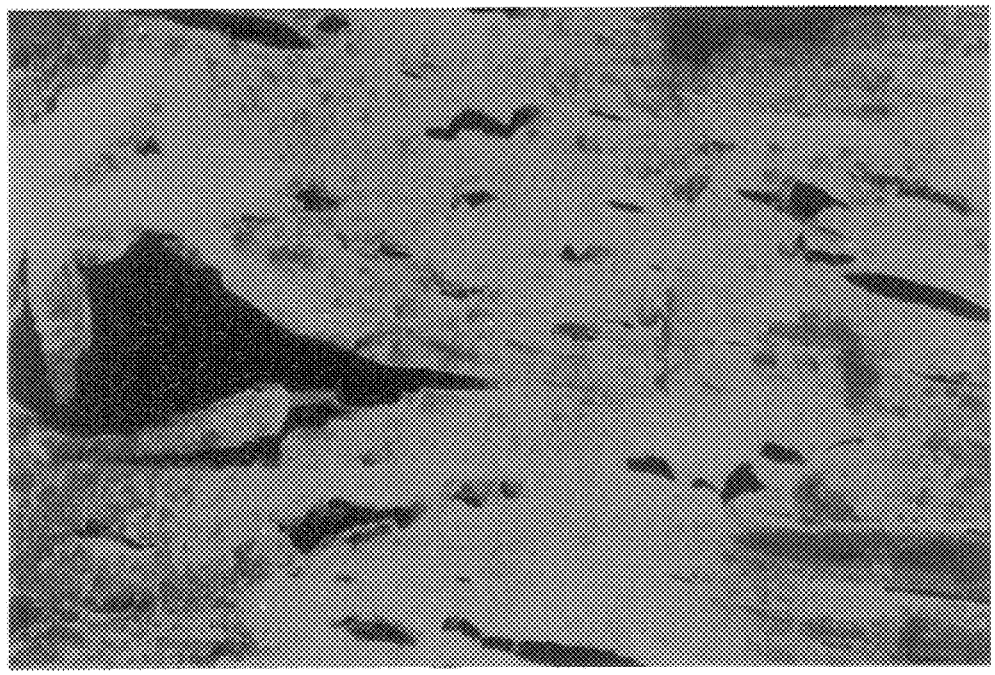
FIG. 10 is a representative fluorescence microscopic images of an experimentally treated specimen at 100× magnification, showing the expression of GFP throughout the tissue.

Results:

Representative fluorescence microscopic images of control and experimental specimens, both at 100× magnification, are illustrated in FIGS. 9 and 10. The control, FIG. 9, shows the expression of GFP only in vessel walls (v) and the immediately surrounding soft tissues (arrows). No GFP expression is seen in adjacent muscle tissues (m). This is in contrast to FIG. 10, which represents the fluorescence microscopic images of the focused ultrasound treated specimen. Here, significant areas of intense fluorescence are seen throughout the muscle parenchyma. These areas represent high levels of transfection of muscle cells with pEGFP-N1 plasmid vector that is mediated by the deposition of focused ultrasound energy.

These results demonstrate that focused ultrasound energy, combined with MR imaging for targeting, can be used to disrupt interstitial integrity for the facilitation of gene transfection in localized sites deep within soft tissue. It is apparent that localized gene therapy, using vectors of various sizes, can be performed in vivo with a high degree of spatial accuracy.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for the targeted in vivo delivery of a compound, the method comprising:
   applying focused ultrasound energy deposition to a target tissue comprising a blood vessel; and
   introducing said compound into said vessel;
   wherein passage of said compound into said tissue is enhanced by targeted changes in said vessel and said tissue.

2. A method according to claim 1, wherein said focused ultrasound energy deposition is image guided.

3. A method according to claim 2, wherein said focused ultrasound energy deposition is guided by magnetic resonance image guidance.

4. A method according to claim 1, wherein said focused ultrasound energy deposition is below the energy level sufficient to cause permanent heat damage.

5. A method according to claim 1 wherein said introducing step comprises injection of said compound immediately following said focused energy deposition.

6. A method according to claim 5, wherein said injection is intramuscular.

7. A method according to claim 5, wherein said injection is intravenous.

8. A method according to claim 5, wherein said injection is intra-arterial.

9. A method according to claim 1, wherein said compound is a pharmacologically active agent.

10. A method according to claim 1, wherein said compound is a liposome.

11. A method according to claim 1, wherein said compound is a nucleic acid.

12. A method according to claim 1, wherein said compound is a protein.

13. A method for the targeted in vivo delivery of a compound, the method comprising:
    applying image guided focused ultrasound to a target tissue, below the energy level sufficient to cause permanent heat damage;
    injecting said compound into said tissue immediately after said applying step;
    wherein passage of said compound into said tissue is enhanced.

14. A method according to claim 13, wherein the application of image guided focused ultrasound is guided by magnetic resonance image guidance.

15. A method according to claim 14, wherein said focused ultrasound is performed with a transducer of from 0.75 to 1.5 MHz, with a diameter from 5 to 15 cm, and a focal length from 5 to 15 cm.

16. A method according to claim 15, wherein said focused ultrasound is from 0.1 to 100 watts/cm$^2$ at target, for 0.01 msec to 100 msec using a duty cycle of from about 0.01 to 100 Hz.

17. A method according to claim 16, wherein said target tissue is muscle.

18. A method according to claim 17, wherein said compound is a pharmacologically active agent.

19. A method according to claim 18, wherein the biologically useful concentration of said agent is enhanced at least about 2 logs relative to the concentration of said agent in the absence of said step of applying image guided focused ultrasound.

* * * * *